United States Patent
Cardinal et al.

(10) Patent No.: US 10,275,881 B2
(45) Date of Patent: Apr. 30, 2019

(54) SEMI-AUTOMATED IMAGE SEGMENTATION SYSTEM AND METHOD

(71) Applicants: ACIST Medical Systems, Inc., Eden Prairie, MN (US); VAL-CHUM, LIMITED PARTNERSHIP, Montreal (CA)

(72) Inventors: Marie-Hélène Roy Cardinal, Québec (CA); François Destrempes, Montréal (CA); Joseph A. Jamello, Saratoga, CA (US); Guy Cloutier, Repentigny (CA); Kendall R. Waters, Livermore, CA (US); Thomas C. Moore, Livermore, CA (US)

(73) Assignees: VAL-CHUM, LIMITED PARTNERSHIP, Montréal, Quebec (CA); ACIST MEDICAL SYSTEMS, INC., Eden Prairie, MN (US)

( * ) Notice: Subject to any disclaimer, the term of this patent is extended or adjusted under 35 U.S.C. 154(b) by 97 days.

(21) Appl. No.: 15/393,430

(22) Filed: Dec. 29, 2016

(65) Prior Publication Data

US 2017/0193658 A1 Jul. 6, 2017

Related U.S. Application Data

(60) Provisional application No. 62/273,610, filed on Dec. 31, 2015.

(51) Int. Cl.
*A61B 5/00* (2006.01)
*G06T 7/00* (2017.01)
(Continued)

(52) U.S. Cl.
CPC .......... *G06T 7/0012* (2013.01); *A61B 5/0066* (2013.01); *A61B 5/0084* (2013.01);
(Continued)

(58) Field of Classification Search
CPC combination set(s) only.
See application file for complete search history.

(56) References Cited

U.S. PATENT DOCUMENTS

| 3,918,025 A | 11/1975 | Koshikawa et al. |
| 4,347,443 A | 8/1982 | Whitney |

(Continued)

FOREIGN PATENT DOCUMENTS

| CN | 101208045 A | 6/2008 |
| CN | 103025247 A | 4/2013 |

(Continued)

OTHER PUBLICATIONS

International Patent Application No. PCT/US2016/069205, International Search Report & Written Opinion dated Mar. 23, 2017, 12 pages.

(Continued)

*Primary Examiner* — Tsung Yin Tsai
(74) *Attorney, Agent, or Firm* — Fredrikson & Byron, P.A.

(57) ABSTRACT

Image segmentation can include a pre-initialization image analysis of image data using an image analysis algorithm to generate a modified image, and the modified image can be presented on a display. An initialization can be performed on the modified image that includes user input on the modified image. The modified image can be segmented using a segmentation algorithm that evaluates the user input. Upon evaluating the user input, the segmentation algorithm can cause a segmented image to be produced which can be presented on the display.

32 Claims, 10 Drawing Sheets

(51) Int. Cl.
  *G06T 7/143* (2017.01)
  *G06T 7/149* (2017.01)
  *A61B 8/12* (2006.01)
  *G06T 7/11* (2017.01)
  *G06T 7/12* (2017.01)

(52) U.S. Cl.
  CPC .................. *A61B 8/12* (2013.01); *G06T 7/11* (2017.01); *G06T 7/12* (2017.01); *G06T 7/143* (2017.01); *G06T 7/149* (2017.01); *G06T 2207/10024* (2013.01); *G06T 2207/10068* (2013.01); *G06T 2207/10101* (2013.01); *G06T 2207/10132* (2013.01); *G06T 2207/20092* (2013.01); *G06T 2207/20101* (2013.01); *G06T 2207/30101* (2013.01)

(56) References Cited

U.S. PATENT DOCUMENTS

| | | | |
|---|---|---|---|
| 4,850,363 A | 7/1989 | Yanagawa | |
| 4,860,758 A | 8/1989 | Yanagawa et al. | |
| 4,949,310 A | 8/1990 | Smith et al. | |
| 5,070,734 A | 12/1991 | Kawabuchi et al. | |
| 5,070,735 A | 12/1991 | Reichert et al. | |
| 5,131,396 A | 7/1992 | Ishiguro et al. | |
| 5,183,048 A | 2/1993 | Eberle | |
| 5,203,338 A | 4/1993 | Jang | |
| 5,363,849 A | 11/1994 | Suorsa et al. | |
| 5,396,285 A | 3/1995 | Hedberg et al. | |
| 5,462,057 A | 10/1995 | Hunt et al. | |
| 5,531,679 A | 7/1996 | Schulman et al. | |
| 5,690,115 A | 11/1997 | Feldman et al. | |
| 5,741,552 A | 4/1998 | Takayama et al. | |
| 5,833,615 A | 11/1998 | Wu et al. | |
| 5,848,969 A | 12/1998 | Panescu et al. | |
| 5,876,343 A | 3/1999 | Teo et al. | |
| 5,921,931 A | 7/1999 | O'Donnell et al. | |
| 6,015,385 A | 1/2000 | Finger et al. | |
| 6,036,650 A | 3/2000 | Wu et al. | |
| 6,132,374 A | 10/2000 | Hossack et al. | |
| 6,139,501 A | 10/2000 | Roundhill et al. | |
| 6,154,572 A | 11/2000 | Chaddha | |
| 6,216,025 B1 | 4/2001 | Kruger | |
| 6,277,075 B1 | 8/2001 | Torp et al. | |
| 6,381,350 B1* | 4/2002 | Klingensmith | A61B 5/02007 382/128 |
| 6,589,181 B2 | 7/2003 | Grunwald et al. | |
| 6,645,147 B1 | 11/2003 | Jackson et al. | |
| 7,194,294 B2 | 3/2007 | Panescu et al. | |
| 7,691,061 B2 | 4/2010 | Hirota | |
| 7,925,064 B2 | 4/2011 | Cloutier et al. | |
| 9,808,222 B2* | 11/2017 | Moore | A61B 8/12 |
| 2001/0017941 A1 | 8/2001 | Chaddha | |
| 2001/0029336 A1 | 10/2001 | Teo | |
| 2003/0063787 A1 | 4/2003 | Natanzon et al. | |
| 2003/0078497 A1 | 4/2003 | Ting et al. | |
| 2003/0097069 A1 | 5/2003 | Avinash et al. | |
| 2003/0191392 A1 | 10/2003 | Haldeman | |
| 2003/0208123 A1 | 11/2003 | Panescu | |
| 2004/0030250 A1 | 2/2004 | Stewart | |
| 2004/0037164 A1 | 2/2004 | Garlick et al. | |
| 2004/0199047 A1 | 10/2004 | Taimisto et al. | |
| 2005/0215897 A1 | 9/2005 | Sakaguchi et al. | |
| 2005/0249391 A1* | 11/2005 | Kimmel | G06T 7/11 382/128 |
| 2006/0253028 A1 | 11/2006 | Lam et al. | |
| 2007/0016068 A1 | 1/2007 | Grunwald et al. | |
| 2007/0036404 A1 | 2/2007 | Li | |
| 2007/0165916 A1* | 7/2007 | Cloutier | A61B 5/02007 382/128 |
| 2007/0167710 A1 | 7/2007 | Unal et al. | |
| 2008/0015569 A1 | 1/2008 | Saadat et al. | |
| 2008/0031498 A1 | 2/2008 | Corcoran et al. | |
| 2008/0200815 A1 | 8/2008 | Van Der Steen et al. | |
| 2008/0234582 A1 | 9/2008 | Nair et al. | |
| 2009/0088830 A1 | 4/2009 | Mohamed et al. | |
| 2009/0284332 A1 | 11/2009 | Moore et al. | |
| 2010/0010344 A1 | 1/2010 | Ahn et al. | |
| 2010/0094127 A1 | 4/2010 | Xu | |
| 2010/0174190 A1 | 7/2010 | Hancock et al. | |
| 2010/0312092 A1 | 12/2010 | Maurice et al. | |
| 2010/0312109 A1 | 12/2010 | Satoh | |
| 2011/0071404 A1 | 3/2011 | Schmitt et al. | |
| 2011/0160586 A1 | 6/2011 | Li et al. | |
| 2011/0257527 A1* | 10/2011 | Suri | A61B 8/0858 600/440 |
| 2012/0065511 A1* | 3/2012 | Jamello, III | A61B 8/0883 600/443 |
| 2012/0123271 A1 | 5/2012 | Cai | |
| 2012/0170848 A1 | 7/2012 | Kemp et al. | |
| 2013/0109968 A1 | 5/2013 | Azuma | |
| 2013/0303907 A1 | 11/2013 | Corl | |
| 2013/0303910 A1 | 11/2013 | Hubbard et al. | |
| 2013/0317359 A1 | 11/2013 | Wilson et al. | |
| 2014/0100440 A1* | 4/2014 | Cheline | A61B 5/02007 600/407 |
| 2014/0180078 A1 | 6/2014 | Nair | |
| 2014/0268167 A1 | 9/2014 | Friedman et al. | |
| 2014/0276065 A1 | 9/2014 | He et al. | |
| 2014/0350404 A1* | 11/2014 | Rajguru | A61B 8/06 600/443 |
| 2015/0099975 A1 | 4/2015 | Lam et al. | |
| 2015/0141832 A1 | 5/2015 | Yu et al. | |
| 2016/0007967 A1* | 1/2016 | Johnson | A61F 2/01 600/424 |
| 2017/0100100 A1 | 4/2017 | Jamello et al. | |
| 2017/0301089 A1 | 10/2017 | Lam et al. | |
| 2017/0330331 A1 | 11/2017 | Bhatt et al. | |
| 2018/0042575 A1 | 2/2018 | Moore et al. | |

FOREIGN PATENT DOCUMENTS

| | | |
|---|---|---|
| EP | 346889 B1 | 1/1995 |
| EP | 851241 A2 | 7/1998 |
| EP | 1387317 A1 | 2/2004 |
| EP | 1609423 A2 | 12/2005 |
| EP | 1988505 A1 | 11/2008 |
| EP | 2488107 A2 | 8/2012 |
| JP | 62221335 A | 9/1987 |
| JP | H09-000522 A | 1/1997 |
| JP | 2001333902 A | 12/2001 |
| JP | 2002530143 A | 9/2002 |
| JP | 2004180784 A | 7/2004 |
| JP | 2006014938 A | 1/2006 |
| JP | 2007029520 A | 2/2007 |
| JP | 2007175542 A | 7/2007 |
| JP | 2007229015 A | 9/2007 |
| JP | 2008508970 A | 3/2008 |
| JP | 2008536638 A | 9/2008 |
| JP | 2009545406 A | 12/2009 |
| JP | 4648652 B2 | 3/2011 |
| JP | 2013507227 A | 3/2013 |
| WO | 0101864 A1 | 1/2001 |
| WO | 2006015877 A1 | 2/2006 |
| WO | 2006113857 A1 | 10/2006 |
| WO | 2006122001 A2 | 11/2006 |
| WO | 2007098209 A2 | 8/2007 |
| WO | 2008016992 A1 | 2/2008 |
| WO | 2008110013 A1 | 9/2008 |
| WO | 2011046903 A1 | 4/2011 |
| WO | 2014186268 A1 | 11/2014 |
| WO | 2017062265 A1 | 4/2017 |
| WO | 2017100274 A1 | 6/2017 |

OTHER PUBLICATIONS

Moore et al., "Intravascular Ultrasound Image Processing of Blood-Filled or Blood-Displaced Lumens," U.S. Appl. No. 15/704,710, filed Sep. 14, 2017, 49 pages.

Dumane et al., "Use of Frequency Diversity and Nakagami Statistics in Ultrasonic Tissue Characterization," IEEE Transactions on

(56) References Cited

OTHER PUBLICATIONS

Ultrasonics, Ferroelectrics, and Frequency Control, vol. 48, No. 5, Sep. 2001, pp. 1139-1146. (cited as Vishruta).

Foster, "Transducer Materials and Probe Construction," Ultrasound in Medicine and Biology, vol. 26, Supp. 1, 2000, pp. S2-S5.

Frijlink et al., "High Frequency Harmonic Imaging in Presence of Intravascular Stents," IEEE Ultrasonics Symposium, 2003, pp. 208-211.

Garcia-Garcia et al., "Imaging of coronary atherosclerosis: intravascular ultrasound," European Heart Journal, vol. 3, 2010, pp. 2456-2469.

Seo et al., "Sidelobe Suppression in Ultrasound Imaging Using Dual Apodization with Cross-Correlation," IEEE Transactions on Ultrasonics, Ferroelectrics, and Frequency Control, vol. 55, No. 10, Oct. 2008, pp. 2198-2210.

Shankar et al., "Computer-Aided Classification of Breast Masses in Ultrasonic B-Scans Using a Multiparameter Approach," IEEE Transactions on Ultrasonics, Ferroelectrics, and Frequency Control, vol. 50, No. 8, Aug. 2003, pp. 1002-1009.

Smith et al., "The Maltese Cross Processor: Speckle Reduction for Circular Transducers," Ultrasonic Imaging, vol. 10, No. 3, Jul. 1988, pp. 153-170.

U.S. Appl. No. 61/218,177, titled Vector Domain Image Enhancement for Mechanically Rotating Imaging Catheters, filed Jun. 18, 2009.

Van Der Steen et al., "IVUS Harmonic Imaging," Ultrasound in Medicine and Biology, vol. 26, Supp. 2, 2000, p. A90.

Wang et al., "Optimizing the Beam Pattern of a Forward-Viewing Ring-Annular Ultrasound Array for Intravascular Imaging," IEEE Transactions on Ultrasonics, Ferroelectrics, and Frequency Control, vol. 49, No. 12, Dec. 2002, pp. 1652-1664.

Waters et al., "Development of a High-Definition Intravascular Ultrasound Imaging System and Catheter," IEEE International Ultrasonics Symposium Proceedings, Oct. 18, 2011, 4 pages.

\* cited by examiner

SEMI-AUTOMATED IMAGE SEGMENTATION SYSTEM AND METHOD

RELATED MATTERS

This application claims the benefit of U.S. Provisional Application No. 62/273,610 filed Dec. 31, 2015, the contents of which are hereby incorporated by reference.

TECHNICAL FIELD

This disclosure relates generally to imaging, and more particularly to image segmentation.

BACKGROUND

Medical imaging techniques generally can be used to collect data and generate in-vivo visualization of anatomical areas of interest. One such example is intravascular imaging, where vascular structures and lumens may be imaged. For instance, intravascular imaging may be used to produce one or more images of the coronary artery lumen, coronary artery wall morphology, and devices, such as stents, at or near the coronary artery wall. Images generated using medical imaging techniques can be useful for diagnostic purposes, such as identifying diagnostically significant characteristics of a vessel.

However, generally information collected during medical imaging can include significant amounts of data, some of which may not be relevant to the purpose for which the imaging is being performed. Consequently, it may be useful to further analyze the data collected and/or image generated during medical imaging so as to simplify image interpretation and automate measurements of clinically useful parameters.

As one example, image segmentation may be used to simplify interpretation and measurement of key features of the image. Image segmentation can be used to partition an image, or set of images, into one or more regions of interest to facilitate the identification of relevant information in the image.

SUMMARY

This disclosure in general relates to image segmentation. Image segmentation can include a pre-initialization image analysis of image data using an image analysis algorithm to generate a modified image, and the modified image can be presented on a display. An initialization can be performed on the modified image that includes a user input on the modified image. Due to the pre-initialization image analysis being performed prior to the initialization, the initialization may require less user interaction and/or take less time. The modified image can be segmented using a segmentation algorithm that evaluates the user input. Upon evaluating the user input, the segmentation algorithm can cause a segmented image to be produced which can be presented on the display.

Examples described in this disclosure may provide one or more advantages over existing systems and methods. For example, the accuracy of the resulting segmented image can be improved while at the same time minimizing time and interaction required from a user. Such benefits are of particular importance in the medical field, which may place constraints on sterile user interaction with a user interface.

Embodiments include devices and systems configured to perform such improved segmentation, computer-readable media capable of executing instructions to perform such improved segmentation, and methods of performing such improved segmentation.

The details of one or more examples are set forth in the accompanying drawings and the description below. Other features, objects, and advantages will be apparent from the description and drawings, and from the claims.

BRIEF DESCRIPTION OF DRAWINGS

The following drawings are illustrative of particular examples of the present invention and therefore do not limit the scope of the invention. The drawings are not to scale (unless so stated) and are intended for use in conjunction with the explanations in the following detailed description. Examples of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Embodiments of the invention include an image segmentation operation useful for displaying a segmented electronic image. Although such an image segmentation operation could be useful in a variety of environments and applications, this disclosure will primarily refer to such image segmentation operations in the context of a user interface for an intravascular imaging system employing intravascular ultrasound (IVUS), optical coherence tomography (OCT), or other suitable imaging techniques used to generate an intravascular image. The disclosed systems and methods may be useful in the medical field where medical equipment often employs user interfaces in a sterile environment.

Figure 1:
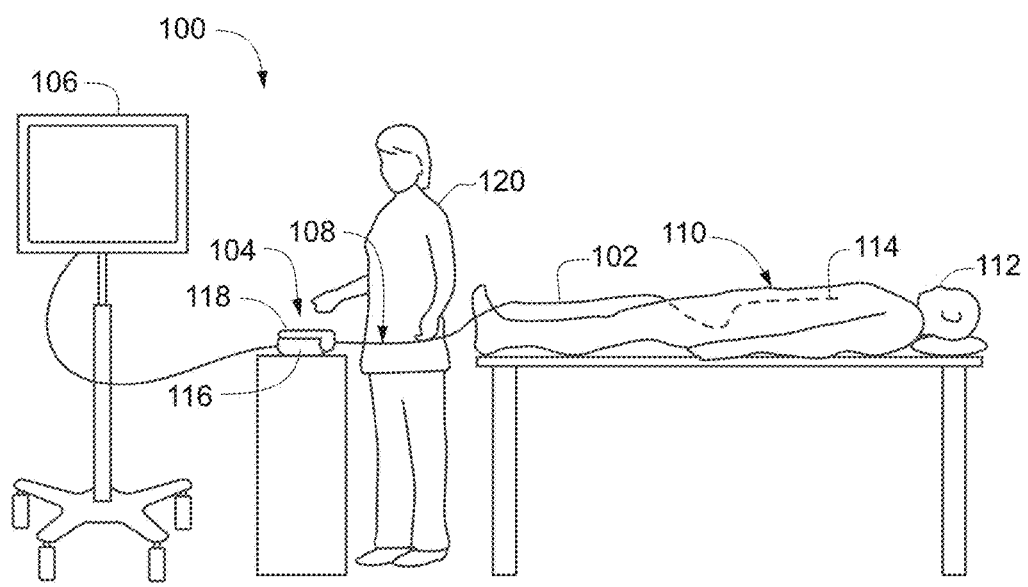
FIG. 1 is an illustrative example of a system configured to perform intravascular imaging.

FIG. 1 illustrates an example of a system 100 that may be configured to perform intravascular imaging. System 100 may include a catheter assembly 102, a translation device 104, and a computing device 106. The catheter assembly 102 may include a proximal end 108 and a distal end 110 configured to be inserted into a vessel of a patient 112. In one application, the catheter assembly 102 may be inserted into the patient 112 via the femoral artery and guided to an area of interest within the patient 112. The broken line in FIG. 1 represents portions of catheter assembly 102 within the patient 112.

In some examples, catheter assembly 102 may include an intravascular imaging device 114 within distal end 110 configured to emit and receive wave-based energy and generate imaging data—e.g., to image the area of interest within the patient 112. For example, where the system 100 is an IVUS system, the intravascular imaging device 114 may comprise an IVUS imaging probe including an ultrasound transducer configured to emit and receive ultrasound energy and generate ultrasound data. In another example, the system 100 may be an OCT system wherein the intravascular imaging device 114 may comprise an OCT imaging probe configured to emit and receive light and generate OCT data. The image data generated by the imaging device 114 can represent a cross-section of an area of interest within the patient 112 at the location of the imaging device 114. The image data generally will represent a plurality of image elements at the cross-sectional location of the imaging device 114, such as, for example, various layers of a vessel of the patient 112 and/or any accumulated matter within the vessel (e.g., plaque).

The translation device 104 may be configured to translate the intravascular imaging device 114 of the catheter assembly 102. The translation device 104 may comprise a linear translation system (LTS) 116. The LTS 116 may be mechanically engaged with the catheter assembly 102 and configured to translate the catheter assembly 102 a controlled distance within the patient 112 during a translation operation, for example a pullback or push-forward operation. In some embodiments, the LTS 116 can be configured so as to both translate the catheter assembly 102 as well as translate the imaging device 114 with respect to the catheter assembly 102. The system 100 may comprise a patient interface module (PIM) 118 configured to interface the translation device 104 with the catheter assembly 102. Translating the imaging device 114 can allow for cross-sectional image data to be collected at various longitudinal locations. This cross-sectional image data at various longitudinal locations can then be compiled to generate a longitudinal cross-sectional image of an area of interest.

The computing device 106 may be in communication with the intravascular imaging device 114 and the translation device 104. According to some examples, the computing device 106 may comprise an imaging engine and a user interface. The imaging engine may include one or more programmable processors and one or more memory modules. One or more programs and/or executable instructions may be stored on the one or more memory modules and be configured to be executed by the one or more processors. The imaging engine may be configured to process imaging data received from the intravascular imaging device 114. For example, the imaging engine may be configured to process the cross-sectional image data received from the imaging device 114 to generate a longitudinal cross-sectional image.

In some examples, the imaging engine may comprise one or more programming modules including, but not limited to, one or more modules for imaging, producing a dynamic user interface, image analysis, and image segmentation. A module for imaging may be adapted to receive imaging data and generate an electronic image based on the imaging data. An image analysis module can be adapted to perform an analysis of the imaging data and electronic image based on the imaging data received by the imaging module using an image analysis algorithm. A user interface module may be adapted to receive inputs from a user, for example from a mouse or a touchscreen, and display an electronic image to the user. In some examples, the interface module may be adapted to detect a motion input from a user. In such examples, an image segmentation module may be adapted to receive the user inputs from the user interface module to cause the interface module to display the electronic image according to a segmentation algorithm that evaluates the user input. Different examples may include other programming modules as suitable for a particular purpose.

In some examples, the computing device 106 may include a user interface configured to receive inputs from a system user 120 and/or display data acquired from the catheter assembly 102. In some examples, the user interface may be in communication with the imaging engine (e.g., the user interface module of the imaging engine) and be configured to display images rendered by the imaging engine. The user interface may comprise any input/output device suitable for a particular application. For example, a user interface may comprise a touchscreen configured to allow the user 120 to interact with a display using, for example, a fingertip, stylus, or other contact point. The touch screen may be of any type including, for example, a resistive touchscreen, a surface acoustic wave touchscreen, or a capacitive touchscreen. In some examples, the user interface may comprise computer peripherals (e.g., mouse and keyboard), software (e.g., voice recognition), or any other suitable devices or programs to receive inputs from the user 120.

Figure 2:
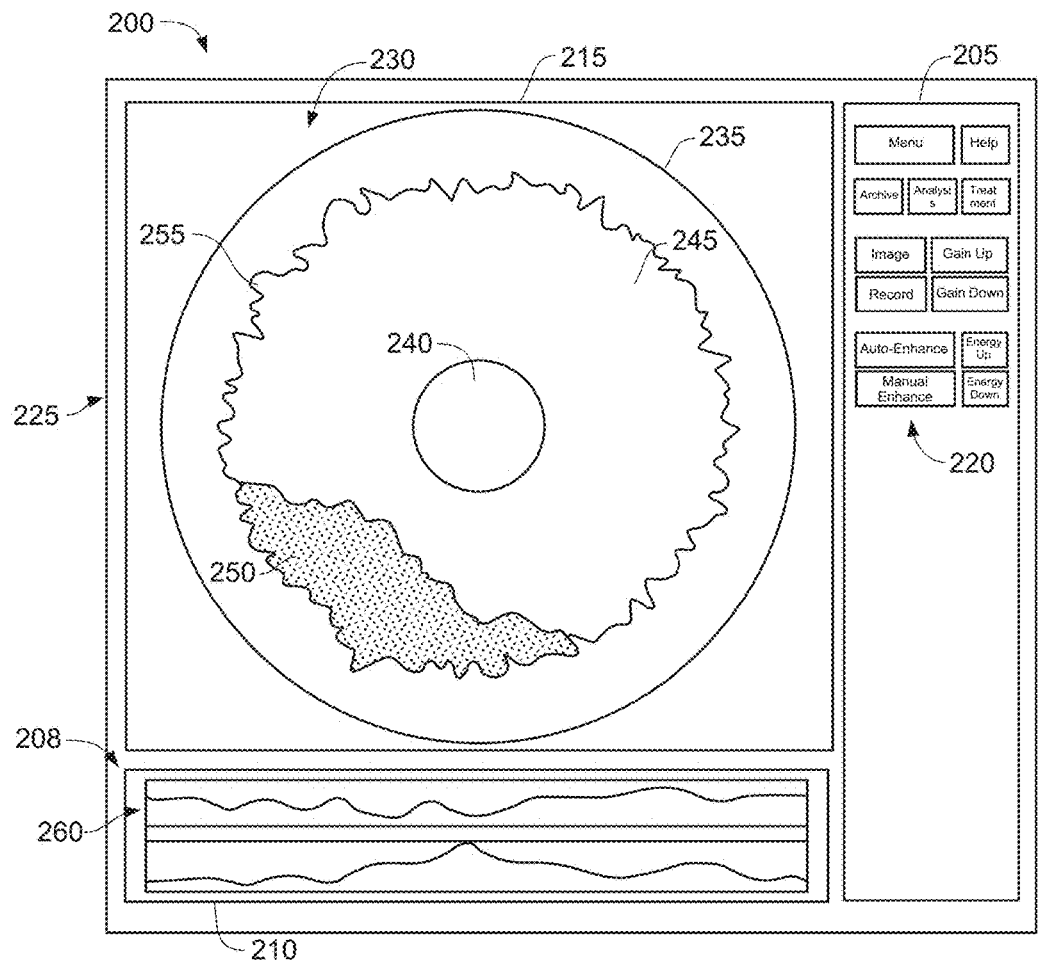
FIG. 2 is an illustrative example of a user interface.

FIG. 2 shows an example of a user interface 200 that may be used in the system 100 as shown and described with respect to FIG. 1. The user interface 200 may comprise a menu 205 and an image display region 208 that includes a first display region 210 and a second display region 215. The menu 205 may be configured to receive inputs from the user and may include selectable graphic icons 220 associated with specific functions or tasks performable by the user interface 200 or an imaging engine in communication with the user interface 200. As noted above, the user interface 200 may be configured to display to a user imaging data received from the imaging device. Imaging data displayed by the user interface 200 may be substantially real-time or stored in one or more memory modules. The first and second display regions 210 and 215 of the image display region 208 may be configured to display imaging data comprising, for example, an image, such as an intravascular image.

In one application of the user interface 200, the second display region 215 may display an electronic image 225 comprising a transverse view cross-section 230 of a vessel 235 of a patient, while the first display region 210 displays a longitudinal view cross-section 260 of the vessel 235. The electronic image 225 may be rendered by an imaging engine with imaging data generated by an intravascular imaging device. In this example, the electronic image 225 includes a focal point of a catheter mask 240 within a vessel lumen 245 of the vessel 235. Display region 208 may be used to help a healthcare professional identify diagnostically significant characteristics of the vessel 235 (e.g., blockages, lesions, location of a stent). For example, the electronic image 225 may show atherosclerotic plaque 250 on a vessel wall 255. The longitudinal view cross-section 260 of the vessel 235 displayed by the first display region 210 can be generated by translating the imaging engine within the vessel 235 to generate a plurality of transverse view cross-sectional images which can be compiled (e.g., by the imaging engine)

to generate the longitudinal view cross-section 260. Thus, the user interface 200 can simultaneously display both one or more transverse view cross-sections 230 and one or more longitudinal view cross-sections 260 on the image display region 208.

The user interface 200 may also be configured to receive inputs from a user. For instance, either or both of the first and second display regions 210 and 215 of the image display region 208 may be configured to receive inputs from a user. Where the first display region 210 is configured to display the longitudinal view cross-section 260, the user input received at the first display region 210 can include, for example, user input indicative of a position within the vessel 235 on the longitudinal view cross-section 260. Then, upon receiving such user input at the first display region 210, the user interface 200 may display the transverse view cross-section 230 of the vessel 235 corresponding to the user input on the longitudinal view cross-section 260 representing the selected position within the vessel 235. This can provide diagnostic benefits as a user is able to survey the vessel 235 of a patient using the longitudinal view cross-section 260 and quickly access a more detailed transverse view cross-section 230 of the vessel 235.

User input received by the image display region 208 (e.g., either or both of the first and second display regions 210 and 215) can additionally include user input indicative of a location of an interface between two layers and/or a layer and a buildup of material within the vessel 235. User input indicative of a location of an interface between two layers and/or a layer and a buildup of material within the vessel 235 can include placement by a user of a control contour and/or a control point on the image display region 208. In one application, upon receiving user input as to a location of an interface between two layers and/or a layer and a buildup of material within the vessel 235 on one of the images 230 or 260, the user interface 200 may display the user inputted location of the interface between two layers and/or a layer and a buildup of material on the other of the cross-sections 230 or 260. For example, in such an application a user may place a control contour along a portion of an interface between two layers of the vessel 235 on the longitudinal view cross-section 260. As a result, the user interface 200 can display a control point corresponding to the location of the control contour on a particular transverse view cross-section 230. This real-time visualization afforded by the user interface 200 of the placed control contour overlaying the longitudinal view cross-section 260 and the corresponding control point overlaying the transverse view cross-section 230 aids in accurately identifying the desired region of interest within the vessel 235.

The user interface 200 can be configured to receive user input based on a motion input from a user (e.g., comprising, consisting, or consisting essentially of a motion input). The motion input may comprise an engage input followed by a motion input, such as a drag motion (e.g., a single drag motion to a disengage point). The motion input can continue until a disengage input is detected. In one example, where the user interface 200 is configured to receive user inputs using a touchscreen, an engage input, a motion input, and a disengage input may comprise touching the touchscreen with a fingertip, stylus, or other contact point, dragging the fingertip, stylus, or other contact point along the surface of the touchscreen, and removing the fingertip, stylus, or other contact point from the surface of the touchscreen, respectively. In another example, where the user interface 200 is configured to receive inputs using a mouse, an engage input, a motion input, and a disengage input may comprise a pressing of a mouse button, a dragging of a mouse while the mouse button is pressed, and a releasing of the mouse button, respectively. Where the user interface 200 is configured to receive user input based on the motion input from the user, the placement of the control contour and/or control point by a user may be accomplished using the motion input.

Figure 3:
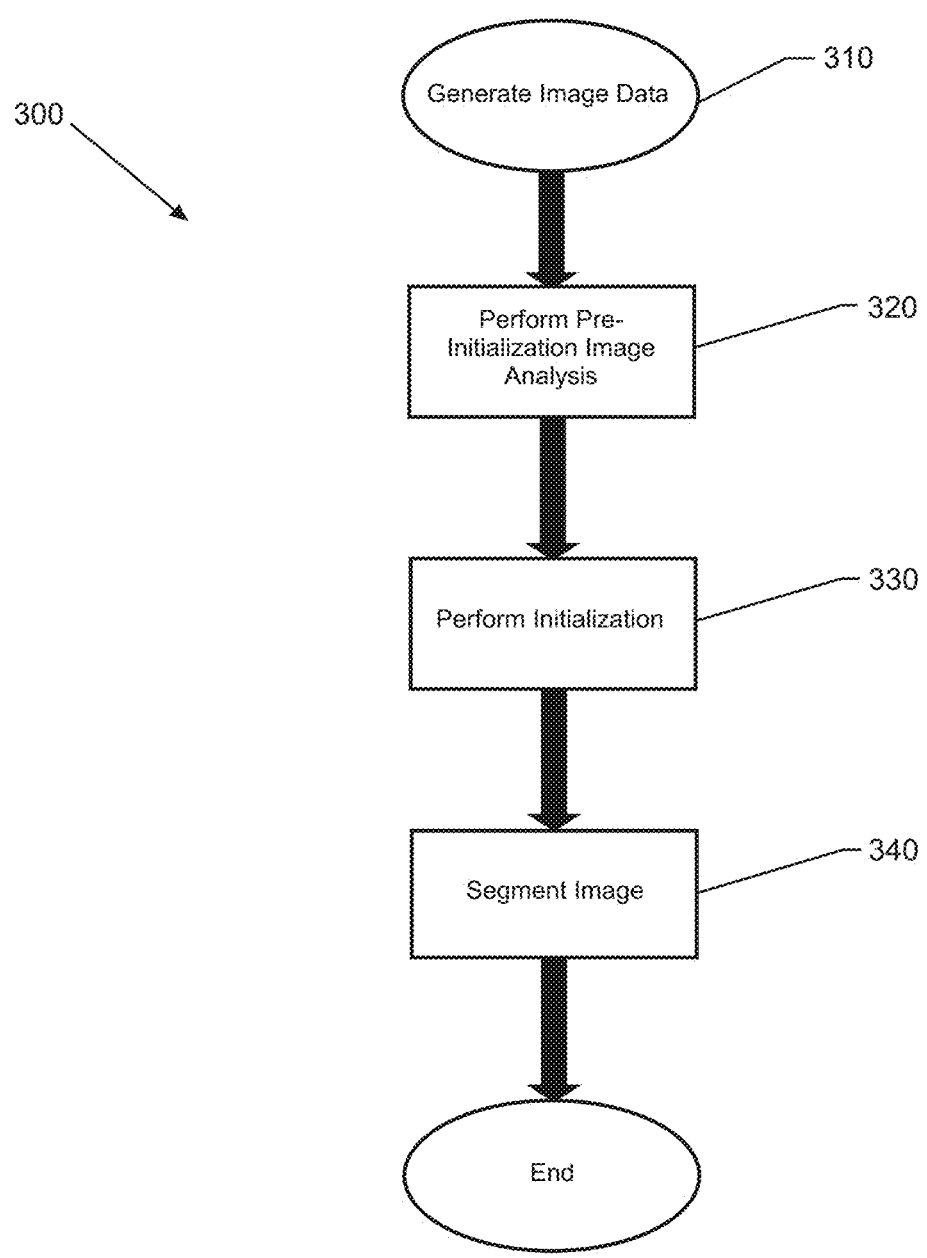
FIG. 3 is a flow diagram illustrating a method of segmenting an image.

FIG. 3 is a flow diagram illustrating a method 300 of segmenting an image. The method 300 will be discussed throughout the remainder of the present description and in conjunction with the description of FIGS. 4-7. The method 300 provides steps for a semi-automated process of image segmentation, as the method 300 includes automated steps and user input steps as part of the process.

In the embodiment of FIG. 3, the method 300 includes initially generating image data in step 310. Image data can be generated in some embodiments using an intravascular imaging system having an intravascular imaging device for emitting and receiving wave-based energy and generating image data based on the received wave-based energy. In some embodiments, the image data can represent a series of cross-sections of a vessel along a longitudinal axis of the vessel. For example, in one application each cross-section can represent a real-time structure of a coronary artery at a particular location. In many instances, however, the image data generated in step 310 may result in cross-sectional images of the vessel which can be difficult to for a user to analyze in raw form. In such cases, the image data generated in step 310 may need to be further processed to increase diagnostic value to a user.

Figure 4:
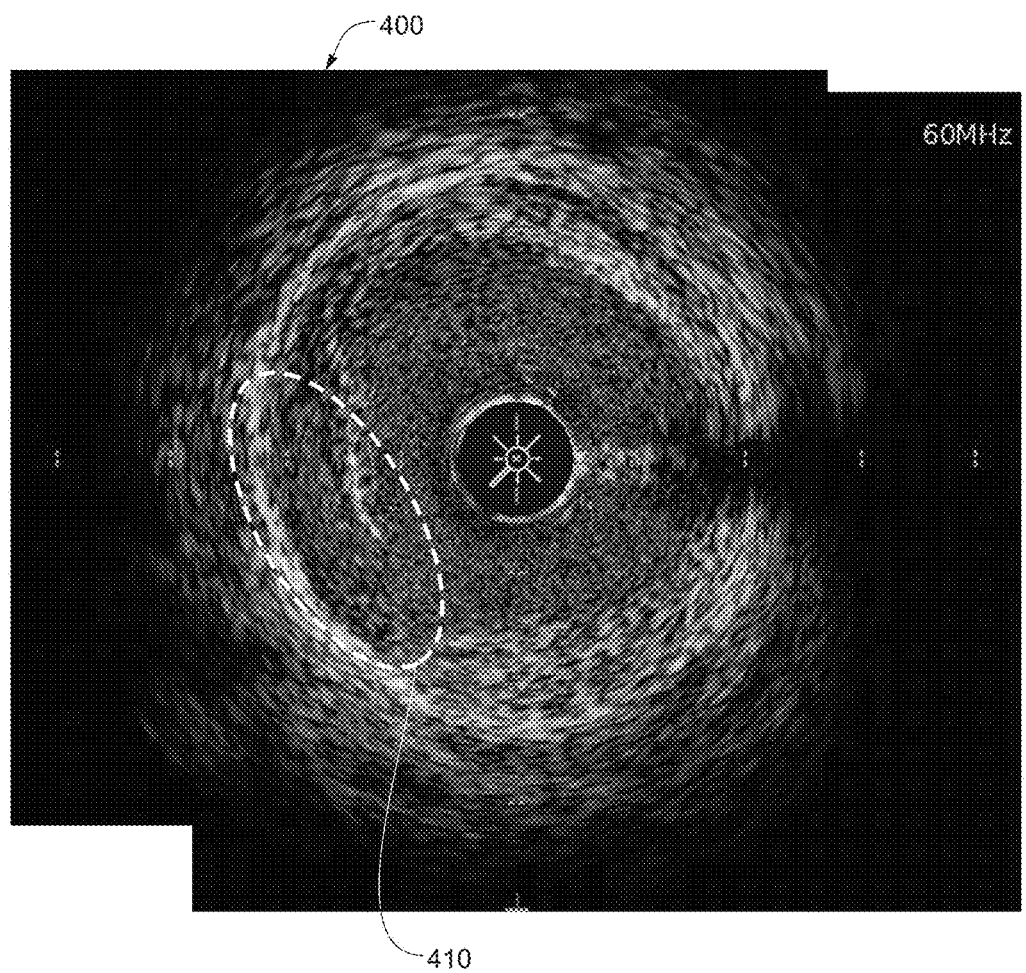
FIG. 4 illustrates a transverse cross-sectional image generated using an intravascular imaging device.

FIG. 4 shows one example of a transverse view cross-sectional image 400 of a vessel of a patient generated using an intravascular imaging device and which may be difficult for a user to analyze. The image data generated in step 310 can be affected by various factors depending on the application. In some applications, such factors can include, for example, electrical noise, thermal noise, relative motion between a vessel and an imaging device within the vessel, and/or speckle. These factors can result in the image containing artifacts and/or appearing blurry. As can be seen, the image data generated for FIG. 4 results in an image 400 that makes it difficult for a user to discern distinct structures or regions of interest within the vessel. For instance, at a region 410 (indicated in this figure with a dashed line) of the image 400 it may be unclear to a user where an interface between two layers of the vessel is located and/or where a buildup of material ends and a vessel layer begins. This can be significant in various applications because, for instance, without being able to identify where one region of interest ends and another region of interest begins any buildup of material within the vessel may not be identified, such as plaque accumulations within a lumen of the vessel. This may result in errors when attempting to measure parameters of interest using the image 400, especially at the indicated region 410.

As shown, the method 300 can include performing a pre-initialization image analysis in step 320. The pre-initialization image analysis may be performed by processing cross-sectional image data generated in step 310 in an image analysis algorithm to generate a modified image. The pre-initialization image analysis can be performed on each cross-sectional image generated in step 310, or in other examples the pre-initialization image analysis can be performed on image data corresponding to predetermined intervals of cross-sectional images (e.g. image data of every hundredth cross-sectional image). This step may run automatically without any involvement of a user. The pre-initialization image analysis of step 320 may act to further clarify the image data generated in step 310, which could otherwise contain artifacts and/or appear blurry, such that the modified image generated using the pre-initialization image analysis in step 320 further defines regions of interest within the vessel relative to the image data generated in step 310.

The image analysis algorithm can employ any useful analyses for analyzing image data to generate a modified image. In some examples, the image analysis algorithm used in step 320 can calculate probability functions. In one example, the image analysis algorithm can include calculating a probability density function of the image data generated in step 310. In applications where the imaging device includes an ultrasound transducer, a mixture of Rayleigh probability density functions can be used in B-mode (brightness modulation) imaging to model a color map distribution of the ultrasonic speckle pattern (e.g., a gray level color map distribution) in a whole cross-sectional image representing a vessel including multiple layers of tissue. In some cases, there can be a mixture of Rayleigh probability density functions, each corresponding to particular structures, such as the lumen, plaque structure of the intima, media, and adventitia including surrounding tissue.

Similarly, in such applications a mixture of Gaussian probability density functions can be used in RF-mode (radio-frequency) imaging to model the color map distribution of the ultrasonic speckle pattern in a whole cross-sectional image representing a vessel including multiple layers of tissue. Again, in some cases there can be a mixture of Gaussian probability density functions, each corresponding to particular structures. This can be repeated for other cross-sectional images generated in step 310 (e.g., at predetermined intervals of cross-sectional images). Another example can include, where the image analysis algorithm used in step 320 calculates a probability density function of the image data generated in step 310, a probability density function model using mixtures of gamma distributions. A mixture of gamma distributions can be used in B-mode imaging to model a color map distribution of the ultrasonic speckle pattern (e.g., a gray level color map distribution) in a whole cross-sectional image representing a vessel including multiple layers of tissue. In some cases, there can be a mixture of gamma probability density functions, each corresponding to particular structures, such as the lumen, plaque structure of the intima, media, and adventitia including surrounding tissue. The description provided here is illustrative, and further examples can include the use of various other distributions, such as the Rician distribution.

Calculating the probability density function in the image analysis algorithm can further include iterative computation techniques of maximum likelihood estimates for any incomplete data (e.g., Expectation-Maximization algorithm) so as to evaluate missing or hidden mixture parameters of the probability density functions, such as to evaluate probability density function mixture parameters. Such iterative computation techniques may be applied to subsets of pixels of a whole cross-sectional image.

As will be appreciated, other estimated gray level probability density functions may be used to generate the modified image. For example, a non-parametric probability density function model for the gray level amplitudes can be adopted. In some applications, such a non-parametric probability density function model can be adopted for desired regions of tissue (e.g., one region representing the guide wire and lumen, a second region representing the intima, a third region representing the media, and a fourth region representing the surrounding tissue).

In another example, the image analysis algorithm used in step 320 can include estimating a distribution color map of cross-sectional image data by calculating a gradient function of the image data. Calculating a gradient function of the image data can involve calculating gray level gradients of a cross-sectional image to discern high and low gradient regions of the image data. Calculating the gradient function of the image data in the image analysis algorithm can allow the modified image to be generated to display further defined structures of the imaged vessel. This can be repeated for other cross-sectional images generated in step 310. As will be appreciated, various other image analysis techniques can be used in step 320 to generate the modified image.

After the modified image is generated by performing the pre-initialization image analysis in step 320, it can be presented, for example, on the user interface. The modified image can include those cross-sectional images upon which the pre-initialization image analysis was performed, as well as the one or more longitudinal cross-sectional images made up of, at least in part, the compiled cross-sectional images upon which the pre-initialization image analysis was performed.

Figure 5:
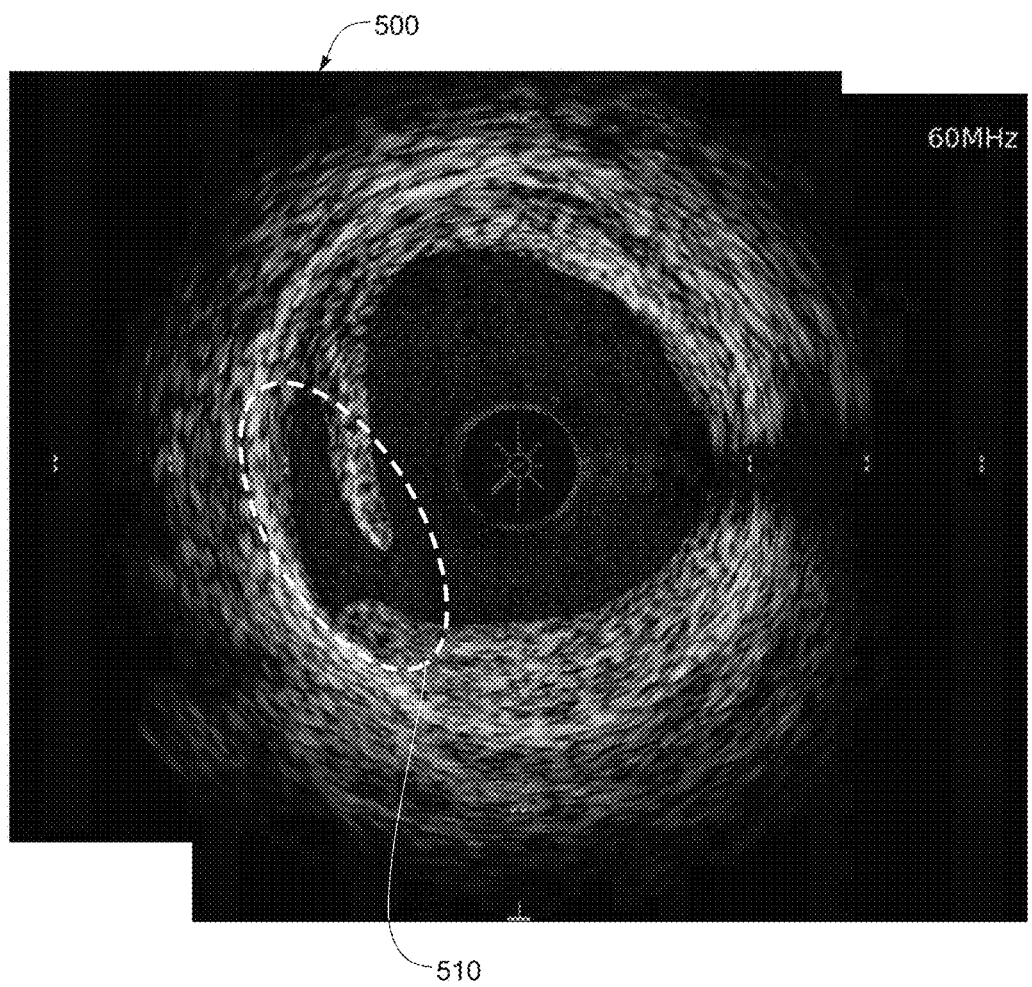
FIG. 5 illustrates a modified transverse cross-sectional image.

FIG. 5 shows an illustrative example of a modified transverse cross-sectional image 500. The modified transverse cross-sectional image 500 is the transverse cross-section image 400 of FIG. 4 after having undergone the pre-initialization image analysis of step 320. As can be seen, the modified cross-sectional image 500 is altered as compared to the cross-sectional image 400 generated using the image data. In one example, the modified cross-sectional image 500 can be altered by being clarified relative to the image generated using the image data. The modified image 500 can be clarified in that, for instance, the modified image 500 illustrates greater contrast between neighboring regions. For instance, the region 510 corresponds to the region 410 of FIG. 4 but as seen in FIG. 5 the region 510 includes greater contrast between neighboring regions, and thus may be easier for a user to analyze. Therefore, by performing the pre-initialization image analysis step 320, the modified image 500 that results can allow a user to timely discern characteristics and/or regions of the vessel being imaged, such as interfaces between layers of the vessel and/or buildup of material within the vessel.

In addition, the modified image 500 may be altered, relative to the image generated using the image data, in some embodiments by including one or more proposed control contours and/or control points placed on a longitudinal and/or cross-sectional image representing one or more regions of interest (shown in subsequent figures). In such examples where the modified image 500 includes one or more proposed control contours and/or control points, the proposed one or more control contours may include one or more visual indicators along a portion of the control contour.

After generating the modified image by performing the pre-initialization image analysis in step 320, an initialization of the modified image can be performed in step 330. FIGS. 6A-6D illustrate examples of modified images that are being initialized. The image 600 is a modified image that has undergone the pre-initialization image analysis of step 320 and is being initialized, such as by receiving a user input. By performing the pre-initialization image analysis of step 320 prior to performing the initialization of step 330, a time required for a user to initialize the modified image can be minimized, for instance, given the enhanced clarity that can be provided by pre-initialization image analysis of step 320.

The initialization of step 330 can include, in various exemplary embodiments, receiving user input in the form of a control contour and/or control point at the region of interest, receiving user input in the form of a confirmation of a proposed control contour (or a portion thereof) and/or control point presented on the modified image 600 as a result of the pre-initialization image analysis of step 320, and/or receiving user input in the form of a modification of a proposed control contour (or a portion thereof) and/or control point presented on the modified image 600 as a result of the pre-initialization image analysis of step 320.

In embodiments where the pre-initialization image analysis of step 320 provides a further defined image 600, a user can more easily recognize desired regions of interest for a particular application and initialize the image by placing one or more control contours and/or control points more accurately at one or more regions of interest with less interaction. Additionally, in embodiments where the pre-initialization image analysis of step 320 generates the modified image to include one or more proposed control contours and/or control points, initialization of the modified image may include receiving confirmation from a user as to the location of the one or more proposed control contours and/or control points. Moreover, even in applications where the one or more proposed control contours and/or control points are not accurately placed at the desired region of interest, initialization of the modified image can include receiving from a user a modification of one or more control contours and/or control points to more accurately locate one or more control contours and/or control points at the desired region of interest. Such applications can allow for timely initialization while improving accuracy by leveraging user expertise when necessary.

In one application, the modified image 600 may be presented on the user interface. The modified image 600 may include both one or more transverse cross-sectional images 605 and one or more longitudinal cross-sectional images 610 of a vessel 615. The cross-sectional image 605 represents a cross-section taken at a particular location in the vessel 615, while the longitudinal cross-sectional image 610 represents a cross-section taken along a longitudinal axis of the vessel 615. The longitudinal cross-sectional image 610 can be constructed using a series of individual cross-sectional images 605 that have undergone the pre-initialization image analysis.

The vessel 615 can be any internal vessel of a patient, such as, for example, a coronary artery. In instances where the vessel 615 is a coronary artery, the vessel 615 can include a blood-filled lumen 620 and a tissue structure 625. The tissue structure 625 can comprise a three-layered wall including, from inner to outer, an intimal layer, media layer, and adventitia layer. In some cases, the plaque 630 may accumulate in the intimal layer of the tissue structure 625. The vessel 615 can also include a catheter assembly 635 present within the lumen 620 for generating image data as described with respect to step 310.

In step 330, an initialization can be performed on the image 600, presented, for example, on the user interface. The initialization can include receiving a user input on the image 600, for instance, on the user interface. In one embodiment, the user input received on the image 600 can include placing a control contour 640 on the image 600. The control contour 640 can be placed along or near any region of interest of the vessel 615 suitable for the particular application. As shown in the illustrative example of FIG. 6, the control contour 640 may be placed along or near an interface of the plaque 630 and the lumen 620 on the longitudinal cross-sectional image 610. This initialization can then be used, as will be described in further detail below, as an input in a segmentation algorithm to segment the image 600 into region(s) of interest.

The user interface and imaging engine can be configured such that as a user inputs the control contour 640 along or near the region of interest on the longitudinal cross-sectional image 610, a control point 645 is generated at a location on the cross-sectional image 605 corresponding to the location of the placed control contour 640 on the longitudinal image 610. This particular cross-sectional image 605 can be displayed simultaneous to the display of the longitudinal image 610 on the user interface. The simultaneously displayed image 605 can be configured to display the control point 645 representing the location of the control contour 640 (placed on the image 610) on the particular image 605. This real-time visualization afforded by the user interface of the placed control contour 640 overlaying the longitudinal cross-sectional image 610 and the corresponding control point 645 overlaying the cross-sectional image 605 aids in accurately initializing the desired region of interest. For instance, if a user notices that the control point 645 on the particular image 605 is not positioned at the desired region of interest, the user can adjust the control contour 640 on the image 610 at the location on the image 610 corresponding to the image 605 to more accurately align the control point 645 at the desired region of interest. This accuracy-verification can be done for any number of particular images 605, and the number of which may vary depending on a level of image data information that was analyzed in the pre-initialization image analysis.

The control contour 640 may be placed on the image 600, such as on the longitudinal cross-sectional image 610, by a user by performing a motion input, such as a single motion input. The single motion input may comprise a single engage input followed by a motion input. The single motion input can continue until a disengage input is detected.

Figure 6A:
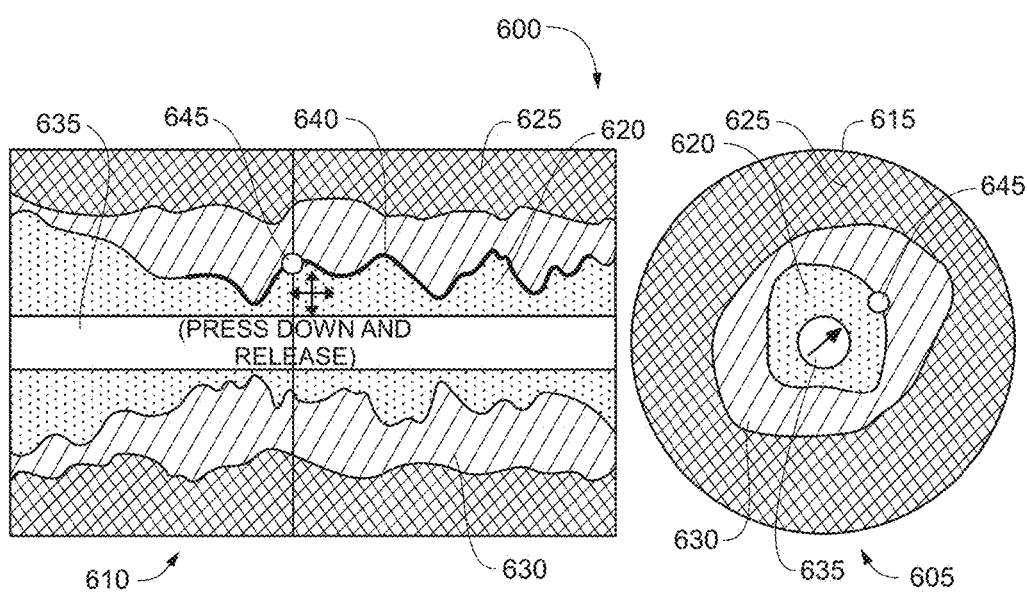
FIG. 6A illustrates an example of an image that has undergone initialization.

In the example of FIG. 6A, the user interface can be configured to receive user input via a mouse. Where a mouse is used to receive user input, an engage input, a motion input, and a disengage input may comprise a pressing and holding of a mouse button, a dragging of a mouse along or near the region of interest on the image 610 while the mouse button is pressed, and a releasing of the mouse button upon arriving at an end of a desired region of interest, respectively. In some embodiments, before the user performs the disengage input, the control contour 640, and thus the corresponding control point 645, can be adjusted by the user while holding the mouse button (e.g., such as when the user notices the control point 645 on a particular image 605 is not accurately placed at the desired region of interest).

Figure 6B:
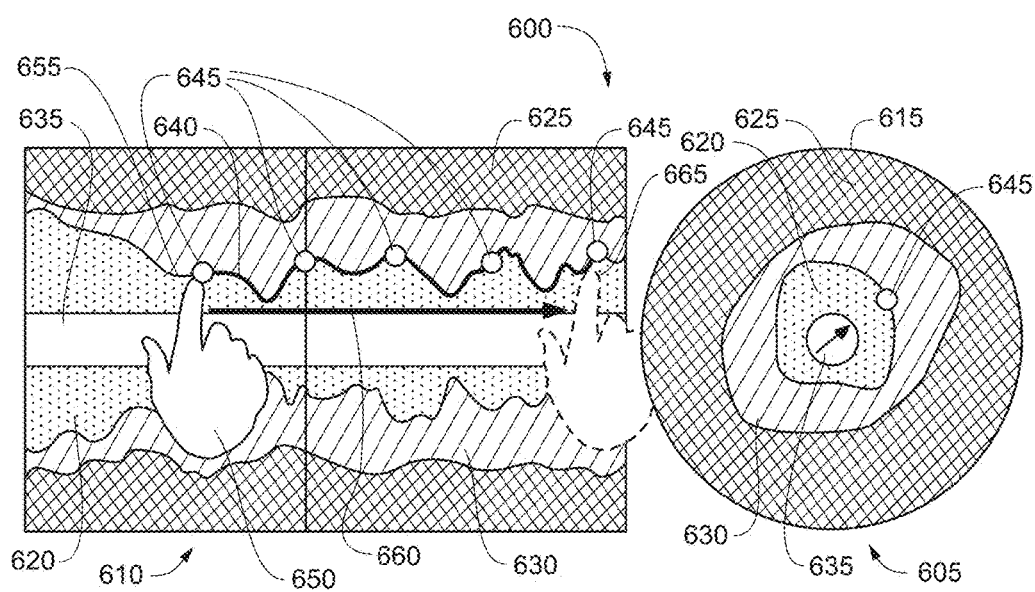
FIG. 6B illustrates an example of an image that has undergone another embodiment of initialization.

In the example shown in FIG. 6B, the user interface may comprise a touchscreen such that the user interface is configured to receive a motion input from a user via a contact point 650 directly on the user interface. The contact point 650 as shown in FIG. 6B is a fingertip, but in other examples the contact point 650 may be a stylus or other contact point.

In the example of FIG. 6B where the user interface can be configured to receive user inputs using a touchscreen, an engage input at 655 of the motion input may comprise touching the touchscreen with the contact point 650 at or near a region of interest to be initialized (e.g. interface of plaque 630 and interior of lumen 620). Upon a user performing the engage input at 655, a motion input at 660 may be performed that comprises a swipe of the contact point 650 along the surface of the touchscreen while the contact point 650 is engaged on the touchscreen. The motion input at 660 can place the control contour 640 on the user interface, such as on the longitudinal cross-sectional image 610, at the desired region of interest. The user interface can be configured, in some embodiments, such that the location of the control contour may be adjusted at all times while the contact point 650 engages the user interface.

As shown in FIG. 6B, the swipe at 660 can be begin at a first point and continue over a distance until to a second point that is spaced from the first point. In some embodiments the swipe at 660 can be in a direction on the touchscreen that is generally horizontal from left to right, or right to left, such that the imaging engine is configured to more accurately place the control contour 640 at the precise region of interest at or near the location of the swipe. In other words, even though the region of interest in some applications is not exactly horizontal from left to right and may have some vertical variations, the user interface can be configured to receive a generally horizontal swipe and place the control contour along the region of interest including any vertical and/or horizontal displacements of the region relative to the location of the swipe. For instance, in one case the swipe at 660 may be in a generally horizontal direction where the longitudinal cross-sectional image is horizontally oriented on the touchscreen (as shown). In another embodiment, the swipe at 660 can be in a direction on the touchscreen that is generally vertical, for example, from a point located at a lower portion of the touchscreen to a point located at an upper portion of the touchscreen (or vice versa). For instance, in one case the swipe at 660 may be in a generally vertical direction where the longitudinal cross-sectional image is vertically oriented on the touchscreen. The location of the user's general motion input during initialization can be used to place the control contour at the region of interest based on the already performed pre-initialization image analysis. If a user discerns that the generally horizontal (or vertical) swipe near the region of interest results in the control contour being positioned at a location different than the desired region of interest, the user can continue to input the engage motion and perform another generally horizontal (or vertical) swipe to cause the user interface to reposition the control contour. In other embodiments, the swipe can be in a direction that follows the region of interest from the engage input location in both horizontal and vertical directions. For example, the swipe at 660 may be in a generally horizontal direction along the touchscreen with vertical variation motion where necessary to conform to the region of interest at which the control contour 640 is being placed.

A disengage input at 665 of the single motion input may comprise removing the contact point 650 from the surface of the touchscreen and may result in placing the control contour 640 at the locations swiped using the contact point 650.

As also shown in FIG. 6B, in some applications the user interface can be configured to generate a plurality of control points 645 along the control contour 640. In one example, control points 645 can be generated on the user interface along the longitudinal cross-sectional image 610 at locations on the image 610 corresponding to cross-sectional images 605 which were generated from information below a threshold level of information as determined by the pre-initialization image analysis. This allows the location of the placed control contour 640 to be investigated at any number of appropriate cross-sectional images 605 efficiently, as those locations most likely to need user verification are identified. As such, real-time visualization of the placed control contour 640 overlaying the longitudinal cross-sectional image 610 and the corresponding plurality of control points 645 overlaying the cross-sectional images 605 aids in accurately initializing the desired region of interest. If a user notices that a control point 645 on a particular cross-sectional image 605 is not accurately located at the region of interest, the user can perform another swipe at the area on the longitudinal image 610 corresponding to the particular cross-sectional image 605 where the control point 645 is inaccurate. This facilitates accurate placement of control points 645 at any or all desired regions of interest.

In various embodiments, the initialization of the modified image may include multiple control contours 640 and corresponding control points 645. In one instance, two control contours 640 can be generated on a modified image where the two control contours 640 are vertically spaced on the longitudinal image from each other so as to be disposed on each side of the region of interest. In this manner, the area within which the region of interest is located can be bounded by the two control contours 640 allowing the segmentation algorithm to evaluate the bounded region for the region of interest. Such bounding of other regions of interest on the same longitudinal image may also be incorporated. Similar to that described above, the control points 645 corresponding to the location of the respective control contours 640 on the cross-sectional image can be investigated to analyze the accuracy of the bounded region of interest.

In some applications, it may be useful to initialize control contours on the longitudinal image in more than one cut-plane taken about the longitudinal image. In some instances, the longitudinal image of a first cut-plane may be disproportionately affected by noise or artifacts, and the effect of such interference can be substantially reduced by generating the longitudinal image about a second, different cut-plane.

Figure 6C:
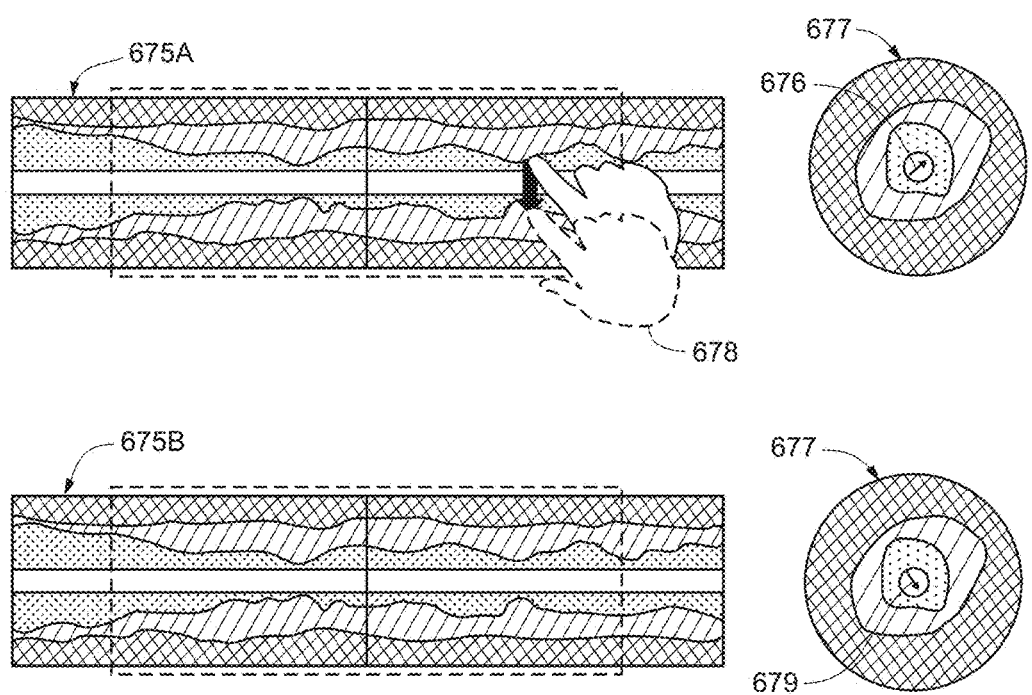
FIG. 6C illustrates an example of an image that has undergone an additional embodiment of initialization.

FIG. 6C shows an embodiment of a longitudinal cross-sectional image 675A taken about a first cut-plane 676 shown relative to the transverse cross-sectional image 677. The images in FIG. 6C are presented after a pre-initialization step and are ready for an initialization step. The transverse cross-sectional image 677 corresponds to the longitudinal cross-sectional image 675 at the location of the user hand 678 on the image 675. Similar to that described previously, one or more control contours can be initialized at one or more regions of interest (e.g., lumen-intima interface) on the image 675A. The longitudinal image 675A taken about the first cut-plane 676 can be rotated to display a second, different cut-plane 679 resulting in the longitudinal cross-sectional image 675B being displayed about the second, different cut-plane 679. In some examples, additional or alternative one or more control contours can be initialized at the same one or more regions of interest relative to that in the image 675A.

In some embodiments, such as where the user interface can be configured to receive user inputs using a touchscreen as described with respect to FIG. 6B, the user interface can be configured to receive the swipe motion input and cause the cut-plane present in the longitudinal cross-sectional image to rotate, such as shown in FIG. 6C. For example, in one application, the rate of rotation of the cut-plane of the longitudinal cross-sectional image can be selected such that as a user makes a swipe motion input (e.g. horizontal from left-to-right along the user interface or vertical from top to bottom along the user interface as shown in FIG. 6C) the cut-plane rotates through a predetermined angle. In the example of FIG. 6C, the cut-plane rotates through a predetermined angle of 90°, as measured from the first cut-plane 676 to the second cut-plane 679. Then, the user can make a swipe motion input in a generally opposite direction (e.g., horizontal from right-to-left along the user interface or vertical from bottom to top along the user interface) that causes the cut-plane of the longitudinal cross-sectional image to rotate an additional predetermined angle, such as 90°, in a same direction of rotation. Both swipes can be continuous such that no disengage motion is received from the user and at any given portion of a swipe the cut-plane of the longitudinal image can be at a different angular position. Thus, in this example the combination of the two horizontal swipe gestures in generally opposite directions can cause the cut-plane of the longitudinal cross-sectional image to continuously rotate through a total of 180°. In another example, the second horizontal swipe in the opposite direction can cause the cut-plane of the longitudinal image to rotate in a direction opposite to the rotational direction brought about by the first horizontal swipe (e.g., 90° during the first swipe, and 90° back to the origin during the second swipe).

The ability to generate a longitudinal cross-sectional image which can be rotated about any desired angular range may reduce the presence of image artifacts that may detrimentally affect the initialization operation. Such image artifacts can, for instance, limit the ability to identify control contours and control points accurately. For example, it may be that in certain applications a particular cut-plane of the longitudinal image initially displayed on the user interface is detrimentally affected by imaging guide wires and/or buildup of calcium or other matter. Thus, rotating the longitudinal cross-sectional image can result in displaying the longitudinal cross-sectional image at an angle where such artifacts do not substantially affect the image. Additionally, this can allow the user to perform initialization, such as placing control contours and/or control points at or near a region of interest, which is not limited to discrete cut-planes and therefore can increase initialization accuracy (e.g., control contours and/or control points at or near a region of interest in a cut-plane with the least interference). Furthermore, configuring the user interface to rotate the cut-plane of the longitudinal image based only one or more continuous, relatively quick swipes by a user may significantly minimize the time needed for initialization.

Figure 6D:
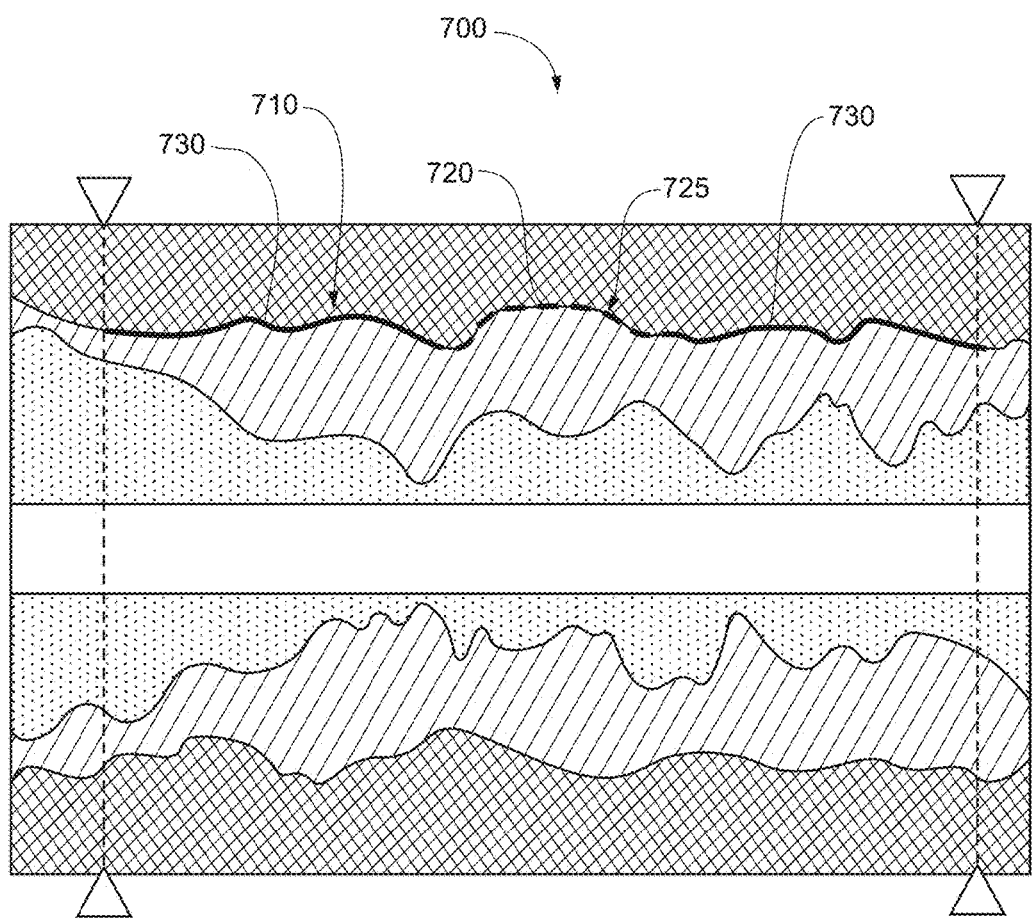
FIG. 6D illustrates an example of an image that has undergone a further embodiment of initialization.

FIG. 6D illustrates an example of another embodiment of a modified image 700 that has been presented after a pre-initialization step and is ready for an initialization step. Image 700 includes a control contour 710 placed along a region of interest as a result of the pre-initialization step 320 (e.g., control contour 710 is displayed automatically on the image 700 as a result of the pre-initialization step 320 without user input). The pre-initialization step 320 can automatically place control contour 710 on the image 700 by estimating a desired region of interest (e.g., a location of an interface between two layers and/or a layer and a buildup of material within the vessel).

In some examples, one or more control contours may be automatically placed at an estimated desired region of interest using of any of the probability functions described previously for pre-initialization step 320, such as probability functions corresponding to the desired region of interest (e.g., corresponding to particular structures, such as the lumen, plaque structure of the intima, media, and adventitia including surrounding tissue). In other examples, in addition to or as an alternative to use of one or more probability density functions, filtering or texture analysis (e.g., gradient filter, Gabor filter, and/or Gamma label map) can be used to automatically place one or more control contours.

As such, when one or more control contours are automatically placed on the image at one or more regions of interest, the initialization step 330 can include, for example, user confirmation of the automatically placed control contour or user modification of one or more portions of the automatically placed control contour. The resulting contour post initialization step 330 can then be used as an input in segmenting the image (step 340).

In the illustrated embodiment of FIG. 6D, the control contour 710 includes a visual indicator 720 along a first portion 725 of the control contour, while a second portion 730 of the control contour 710 does not include a visual indicator. A visual indicator can comprise any visual distinction of a portion of a control contour 710 relative to another portion or portions of the control contour 710. As shown, the visual indicator 720 is a dashed line along the first portion 725 of the control contour 710, while the second portion 730 of the control contour 710 is a solid line. In other examples, the visual indicator can be other line patterns and/or various colors that are different from that used on another portion of the control contour.

The pre-initialization analysis algorithm may be configured to generate a visual indicator 725 for one or more portions of the control contour 710 where that portion of the control contour 710 is generated from information below a threshold level of information. Information below a threshold level of information can include in some applications, for example, a low signal-to-noise ratio of the image data corresponding to the cross-sectional images representative of the respective portion of the control contour. In one application, the threshold level of information can be a signal-to-noise ratio of, e.g., 6 dB, such that any portion of the control contour generated from information having a signal-to-noise ratio below 6 dB will be displayed using a visual indicator. In another application, the threshold level of information can be a signal-to-noise ratio of, e.g., 12 dB, such that any portion of the control contour generated from information having a signal-to-noise ratio below 12 dB will be displayed using a visual indicator. In other applications, various signal-to-noise ratios can be used as the threshold level as is suitable for a desired application, which may take into account the level of accuracy needed for the desired application, the amount of time available, and/or the degree of user interaction permitted by the application.

By displaying the visual indicator 725 at one or more locations along the control contour 710 where the image displayed on the user interface is generated from information below a threshold level of information, a user can be alerted that such a portion of the control contour may be desirable to investigate further for accuracy and may be desirable to provide further user input at this location. Thus, this can allow a user to leverage expertise for the portions which could benefit from such expertise, while not requiring time be spent investigating other portions of the control contour 710 which are based on greater levels of information. Also, displaying the visual indicator 725 at one or more locations along the control contour 710 where the image displayed on the user interface is generated from information below a threshold level of information can allow a user to selectively choose which image, or portions of images, to be used as inputs in the segmentation step (step 340). For instance, in one embodiment images lacking a visual indicator may be beneficial to use as the sole inputs for the segmentation step. Thus, the use of a visual indicator may guide a user is choosing reliable images, or portions of images, for segmentation and thus quantitative measurements. This can increase the accuracy of the resulting measurements.

In other embodiments, one or more visual indicators can be used to convey a range of certainty to a user corresponding to the respective one or more portions of the control contour that is displayed using the visual indicator. For example, a spectrum of various colors can be used as visual indicators, where colors at or near one end of the spectrum correspond to varying degrees of relatively low levels of information upon which the control contour was generated (and thus lower levels of certainty for that portion of the control contour) and colors at or near an opposite end of the spectrum correspond to varying degrees of relatively high levels of information upon which the control contour was generated (and thus higher levels of certainty for that portion of the control contour). In one application, a red visual indicator can be displayed along a portion of a control contour that is based on a low level of information. In addition, a yellow visual indicator can be displayed along a portion of a control contour that is based on a low level of information, but such level of information is greater than the level of information resulting in the red visual indicator. Similarly, a violet visual indicator can be displayed along a portion of a control contour that is based on a high level of information. In addition, a blue visual indicator can be displayed along a portion of a control contour that is based on a high level of information, but such level of information is less than the level of information resulting in the violet visual indicator.

As will be appreciated, the initialization step 330 may include the placement, modification, and/or confirmation of any number of control contours and/or control points, at any number of regions of interest. For example, in one application a user may cause the user interface to receive one or more control contours for each of two or more regions of interest.

After having initialized the image in step 330, the image can be segmented in step 340. Segmenting the image in step 340 can include using a segmentation algorithm that incorporates the user input received during the initialization (e.g., user input in the form of a control contour and/or control point at a region of interest, receiving user input in the form of a confirmation of a proposed control contour (or a portion thereof) and/or control point presented on the modified image 600 as a result of the pre-initialization image analysis of step 320, and/or receiving user input in the form of a modification of a proposed control contour (or a portion thereof) and/or control point presented on the modified image 600 as a result of the pre-initialization image analysis of step 320). For example, the segmentation algorithm may evaluate the control points initialized at the region of interest on the cross-sectional images (e.g., resulting from the user placing the control contour on, for example, the longitudinal image), such as by using the control points as an input in the segmentation algorithm.

The segmentation algorithm can be used to identify any desired region of interest initialized by a user. For example, in one application the segmentation algorithm can use the user input during initialization to identify a lumen-intima interface in a vessel, a media-adventitia interface in a vessel, and/or an interface between a buildup of plaque and an interior volume of a lumen. Segmenting the image in step 340 can result in the image being partitioned into one or more desired regions of interest to facilitate diagnostic analysis by a medical professional. The segmented image may be presented on a display, such as the user interface, to facilitate diagnostic analysis.

In one embodiment, the segmentation can be performed using a fast marching model (FMM) based on a probability function, such as the FMM described in U.S. Pat. No. 7,925,064, the contents of which are hereby incorporated by reference. The FMM can operate to find a boundary between two regions, such as by using two bounding interfaces each moving in opposite directions toward a common boundary. A speed function can be associated with each interface for the rate of movement toward the boundary. When using the FMM, the one or more desired regions of interest (e.g., boundary between external elastic membrane and adventitia and/or boundary between lumen and intima) can be provided as outputs, and may for instance be modeled as layered contours that each propagate under a speed function in the FMM. The FMM can construct an arrival time function for each speed function such that when the two interfaces have met at the boundary the associated speed functions are minimal. The one or more control contours and/or control points resulting from the initialization step may be used as the boundary. The FMM can be applied to each desired image for defining the relevant one or more areas of interest in such images.

Figure 7:
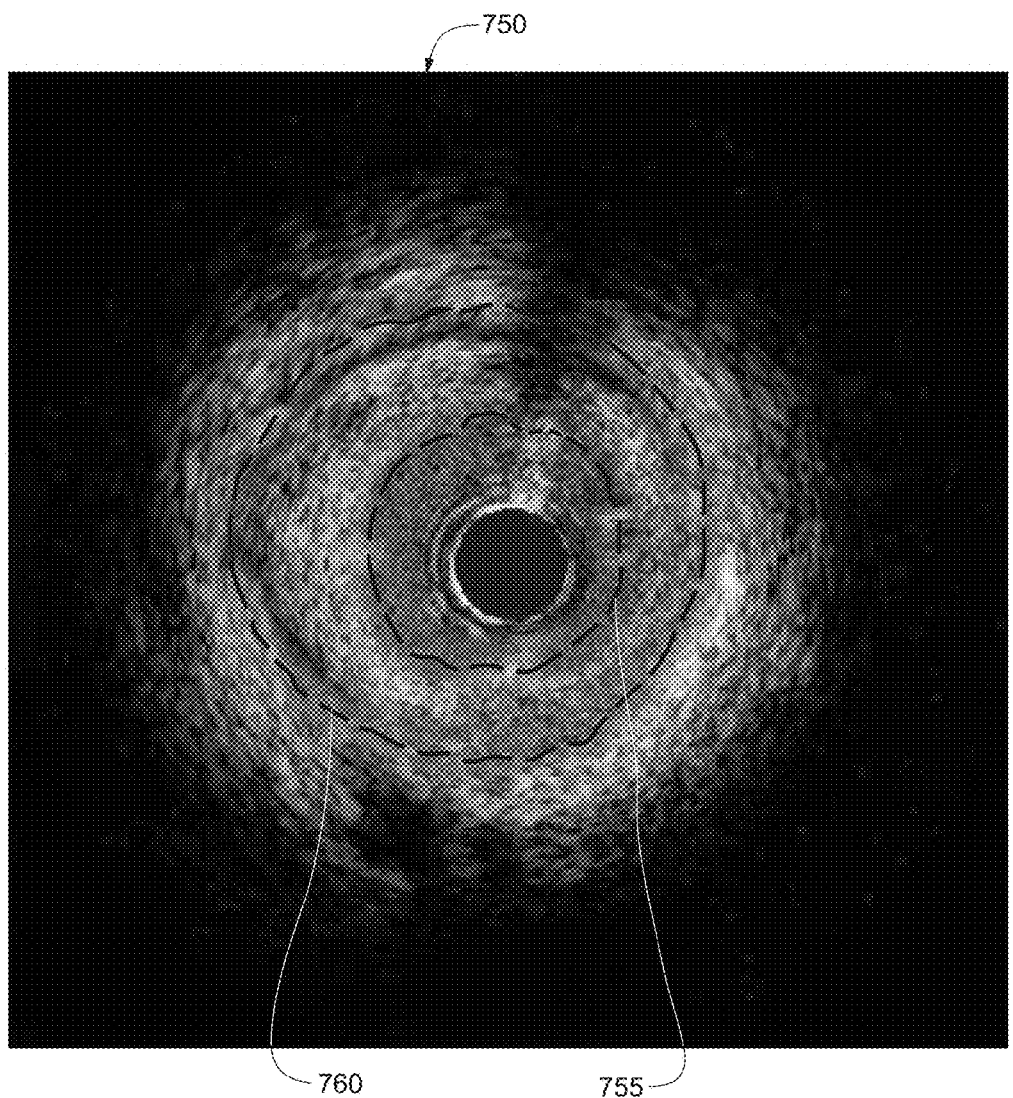
FIG. 7 illustrates an example of a transverse cross-sectional segmented image.

FIG. 7 shows an example of a segmented transverse cross-sectional image 750 having segmented contours 755 and 760. One or more of the segmented contours 755, 760 can be displayed using a color map based on values of the speed function of the FMM at each point on the respective segmented contours 755, 760. For instance, in the example of FIG. 7 where the segmented contour 755 corresponds to a boundary between the lumen and intima the color value is displayed to correspond to the value of the speed functions at each pixel of the contour 755. Similarly, in this example where the segmented contour 760 corresponds to a boundary between the external elastic membrane and adventitia the color value is displayed to correspond to the value of the speed function at each pixel of the contour 760. Displaying a segmented contour 755 and/or 760 with a color map can provide a visual indication as to a measure of certainty on each portion of the segmented contour. Indeed, the goal of the FMM algorithm can be to compute the optimal segmented contour where the speed function has minimal values, such as close to zero. Thus, the use of a color map as part of the displayed segmented contour can provide a user a warning produced by the FMM algorithm as to which portion(s) of the segmented contour may be less reliable (e.g., where the corresponding speed function value at such location on the contour exceeds a predetermined value above or below zero).

Other embodiments may include a method of segmenting an image, where the method includes a user performing, or causing to be performed, a pre-initialization image analysis of image data to generate a modified image. The user can generate the image data using an intravascular imaging system, and the image data may represent a plurality of image elements. The user can perform, or cause to be performed, the pre-initialization image analysis using an image analysis algorithm. After performing, or causing to be performed, the pre-initialization image analysis, the user can perform initialization of the modified image. The user may perform the initialization of the modified image by inputting information, such as a user confirmation or control contour, on the modified image. After the user has performed the initialization, the user can segment, or cause to be segmented, the modified image. The user can segment, or cause to be segmented, the modified image by evaluating the inputted information in a segmentation algorithm. The user can display, or cause to be displayed, a segmented image.

A further embodiment can include an imaging system. The system may include a catheter assembly with an intravascular imaging device to generate imaging data. The image data generated by the catheter assembly can represent a plurality of image elements. The system may also include a user interface having an image display region. In some examples, the user interface can be configured to receive inputs from a user, and may include, at least in part, one or more touchscreens. The system can further include an imaging engine in communication with the intravascular imaging device and the user interface.

The imaging engine may have at least one processor. The imaging engine can be configured to receive the image data generated by the catheter assembly and perform a pre-initialization image analysis of the image data using the at least one processor. The imaging engine may perform the pre-initialization image analysis using an image analysis algorithm. The imaging engine can then generate a modified image on the image display region. Once the modified image has been generated, the imaging engine may receive inputs from the user on the modified image. The imaging engine can then use the at least one processor to initialize the modified image to include the received user input. The imaging engine may then segment the modified image using a segmentation algorithm. The segmentation algorithm used by the imaging engine can evaluate the received user input on the modified image. The imaging engine may then cause a segmented image to be displayed on the image display region.

Another embodiment can include a non-transitory computer-readable storage article having computer-executable instructions sorted thereon to cause at least one programmable processor to perform a pre-initialization image analysis of image data. The image data may represent a plurality of image elements. The pre-initialization image analysis can be performed by the at least one programmable processor using an image analysis algorithm to generate a modified image on a display. Additionally, the at least one programmable processor can perform an initialization of the modified image generated from the pre-initialization image analysis. The initialization performed by the at least one programmable processor can include receiving user input and causing the user input to be displayed on the modified image on the display. The at least one programmable processor may then segment the modified image using a segmentation algorithm. The segmentation algorithm can evaluate the received user input. The at least one programmable processor may the cause a segmented image to be displayed.

Various examples of the invention have been described. Although the present invention has been described in considerable detail with reference to certain disclosed embodiments, the embodiments are presented for purposes of illustration and not limitation. Other embodiments incorporating the invention are possible. One skilled in the art will appreciate that various changes, adaptations, and modifications may be made without departing from the spirit of the invention and the scope of the appended claims.

The invention claimed is:

1. A method of segmenting an image, the method comprising the steps of:
    performing a pre-initialization image analysis of image data using an image analysis algorithm to generate a modified image and presenting the modified image on a display, wherein the image data represents a plurality of image elements;
    performing an initialization of the modified image generated by the pre-initialization image analysis, wherein performing the initialization includes receiving a user input on the modified image on the display; and
    segmenting the modified image using a segmentation algorithm that evaluates the received user input of the performed initialization and displaying a segmented image on the display,
    wherein the modified image includes a proposed control contour and the proposed control contour on the modified image on the display comprises a first visual indicator along a first portion of the proposed control contour and a second visual indicator along a second portion of the proposed control contour, wherein the first and second visual indicators are different and one of the first and second visual indicators designates that the respective portion of the proposed control contour is below a threshold level of information determined by the pre-initialization image analysis, and
    wherein the second visual indicator along the second portion of the proposed control contour designates that the second portion of the proposed control contour is below a threshold level of information, and wherein the second visual indicator comprises one of a color different from a color of the first visual indicator and a line pattern different from a line pattern of the first visual indicator.

2. The method of claim 1, further comprising:
    generating the image data used in the pre-initialization image analysis representing the plurality of image elements with an intravascular ultrasound imaging system.

3. The method of claim 2, wherein generating the image data with the intravascular ultrasound imaging system comprises:
    collecting cross-sectional image data using a catheter assembly that includes an intravascular imaging device having an imaging module for emitting and receiving energy.

4. The method of claim 3, wherein the intravascular imaging device comprises an ultrasound transducer configured to emit and receive ultrasound energy.

5. The method of claim 1, wherein the image analysis algorithm includes calculating a probability density function of the image data.

6. The method of claim 1, wherein the image analysis algorithm includes calculating a gradient function of the image data.

7. The method of claim 1, wherein the modified image is clearer relative to an image generated using the image data before the pre-initialization image analysis of the image data is performed.

8. The method of claim 1, wherein receiving the user input on the modified image on the display comprises receiving a confirmation of a proposed control contour, or a portion thereof, presented on the modified image on the display.

9. The method of claim 1, wherein receiving the user input on the modified image on the display comprises receiving a modification of a proposed control contour, or a portion thereof, presented on the modified image on the display.

10. The method of claim 1, wherein receiving the user input on the modified image on the display comprises receiving a control contour placed on the modified image on the display.

11. The method of claim 10, wherein the control contour is placed at or near a location of a lumen-intima interface on the modified image on the display.

12. The method of claim 10, wherein the control contour is placed at or near a location of a media-adventitia interface on the modified image on the display.

13. The method of claim 10, wherein the control contour is placed on a longitudinal image on the display and a first control point is generated on a first cross-sectional image on the display, wherein the first control point corresponds to a location of the control contour on the first cross-sectional image.

14. The method of claim 13, wherein the first control point is generated on the longitudinal image on the display and a second control point is generated on the longitudinal image on the display, wherein the second control point corresponds to a location of the control contour on a second cross-sectional image, and wherein the first cross-sectional image and the second cross-sectional image are spaced apart along the longitudinal image by a predetermined interval of cross-sectional images.

15. The method of claim 1, wherein the threshold level of information determined by the pre-initialization image analysis comprises a signal-to-noise ratio of the image data, and wherein the second visual indicator designates that the respective portion of the proposed control contour is below the threshold level signal-to-noise ratio of the image data.

16. The method of claim 1, wherein the image analysis algorithm increase contrast between neighboring image elements in the image data, wherein the modified image is presented on the display with the increased contrast between neighboring image elements, wherein the initialization is performed after the pre-initialization image analysis, and wherein the segmenting is performed after the initialization.

17. A method of segmenting an image, the method comprising the steps of:
performing a pre-initialization image analysis of image data using an image analysis algorithm to generate a modified image and presenting the modified image on a display, wherein the image data represents a plurality of image elements;
performing an initialization of the modified image generated by the pre-initialization image analysis, wherein performing the initialization includes receiving a user input on the modified image on the display; and
segmenting the modified image using a segmentation algorithm that evaluates the received user input of the performed initialization and displaying a segmented image on the display,
wherein the modified image includes a proposed control contour and the proposed control contour on the modified image on the display comprises a first visual indicator along a first portion of the proposed control contour and a second visual indicator along a second portion of the proposed control contour, wherein the first and second visual indicators are different and one of the first and second visual indicators designates that the respective portion of the proposed control contour is below a threshold level of information determined by the pre-initialization image analysis, and
wherein the threshold level of information determined by the pre-initialization image analysis comprises a signal-to-noise ratio of the image data, and wherein one of the first and second visual indicators designates that the respective portion of the proposed control contour is below the threshold level signal-to-noise ratio of the image data.

18. The method of claim 17, wherein the one of the first and second visual indicators that designates that the respective portion of the proposed control contour is below the threshold level signal-to-noise ratio of the image data comprises one of a different color and a line pattern.

19. The method of claim 17, wherein the image analysis algorithm increase contrast between neighboring image elements in the image data, wherein the modified image is presented on the display with the increased contrast between neighboring image elements, wherein the initialization is performed after the pre-initialization image analysis, and wherein the segmenting is performed after the initialization.

20. The method of claim 17, wherein the image analysis algorithm includes calculating a probability density function of the image data.

21. The method of claim 17, wherein the image analysis algorithm includes calculating a gradient function of the image data.

22. The method of claim 17, wherein the modified image is clearer relative to an image generated using the image data before the pre-initialization image analysis of the image data is performed.

23. The method of claim 17, wherein the proposed control contour is placed on a longitudinal image on the display and a first control point is generated on a first cross-sectional image on the display, wherein the first control point corresponds to a location of the proposed control contour on the first cross-sectional image.

24. The method of claim 23, wherein the first control point is generated on the longitudinal image on the display and a second control point is generated on the longitudinal image on the display, wherein the second control point corresponds to a location of the proposed control contour on a second cross-sectional image, and wherein the first cross-sectional image and the second cross-sectional image are spaced apart along the longitudinal image by a predetermined interval of cross-sectional images.

25. A non-transitory computer-readable storage article having computer-executable instructions stored thereon to cause at least one programmable processor to:
perform a pre-initialization image analysis of image data using an image analysis algorithm to generate a modified image and present the modified image on a display, wherein the image data represents a plurality of image elements, wherein the image analysis algorithm increases contrast between neighboring image elements in the image data, and wherein the modified image is presented on the display with the increased contrast between neighboring image elements;
after the pre-initialization image analysis, perform an initialization of the modified image generated by the pre-initialization image analysis, wherein the initialization includes receiving a user input on the modified image on the display; and
after the initialization of the modified image, segment the modified image using a segmentation algorithm that evaluates the received user input of the initialization and display a segmented image on the display.

26. The article of claim 25, wherein the image analysis algorithm includes calculating a probability density function of the image data.

27. The article of claim 25, wherein the received user input on the modified image on the display comprises a control contour placed on the modified image on the display.

28. The article of claim 25, wherein the modified image includes a proposed control contour and the proposed control contour on the modified image on the display comprises a first visual indicator along a first portion of the proposed control contour and a second visual indicator along a second portion of the proposed control contour, wherein the first and second visual indicators are different and one of the first and second visual indicators designates that the respective portion of the proposed control contour is below a threshold level of information determined by the pre-initialization image analysis.

29. The article of claim 28, wherein the second visual indicator along the second portion of the proposed control contour designates that the second portion of the proposed control contour is below a threshold level of information, and wherein the second visual indicator comprises one of a color different from a color of the first visual indicator and a line pattern different from a line pattern of the first visual indicator.

30. The article of claim 28, wherein the threshold level of information determined by the pre-initialization image analysis comprises a signal-to-noise ratio of the image data, and wherein one of the first and second visual indicators designates that the respective portion of the proposed control contour is below the threshold level signal-to-noise ratio of the image data.

31. The article of claim 28, wherein the proposed control contour is placed on a longitudinal image on the display and a first control point is generated on a first cross-sectional image on the display, wherein the first control point corresponds to a location of the proposed control contour on the first cross-sectional image.

32. The article of claim 31, wherein the first control point is generated on the longitudinal image on the display and a second control point is generated on the longitudinal image on the display, wherein the second control point corresponds to a location of the proposed control contour on a second cross-sectional image, and wherein the first cross-sectional image and the second cross-sectional image are spaced apart along the longitudinal image by a predetermined interval of cross-sectional images.

* * * * *